United States Patent [19]

Mizia et al.

[11] Patent Number: 5,021,590

[45] Date of Patent: Jun. 4, 1991

[54] PROCESS FOR PRODUCING N-ALKYL-CARBAMATES

[75] Inventors: Franco Mizia, Milan; Franco Rivetti, Schio; Ugo Romano, Vimercate, all of Italy

[73] Assignee: Enichem Synthesis SpA, Palermo, Italy

[21] Appl. No.: 485,858

[22] Filed: Feb. 22, 1990

Related U.S. Application Data

[63] Continuation of Ser. No. 220,463, Jul. 18, 1988, abandoned.

[30] Foreign Application Priority Data

Jul. 31, 1987 [IT] Italy ................................ 21561 A/87

[51] Int. Cl.$^5$ ................ C07D 317/64; C07D 307/78; C07C 125/067
[52] U.S. Cl. ................................ 549/438; 549/470; 560/136; 560/135; 560/134; 560/132

[58] Field of Search ............... 560/132, 134, 135, 136; 549/470, 438

[56] References Cited

U.S. PATENT DOCUMENTS 4,390,710 6/1983 Manner ............................... 549/441

FOREIGN PATENT DOCUMENTS 0200429 11/1986 European Pat. Off. .

*Primary Examiner*—Nicky Chan
*Attorney, Agent, or Firm*—Hedman, Gibson, Costigan & Hoare

[57] ABSTRACT

A process is provided for the preparation of N-alkyl-carbamates by directly reacting low-molecular weight alkyl-isocyanates, in particular methyl isocyanate, and a substituted phenolic precursor in solution in the presence of a basic catalyst compound selected from the class of bicyclic amidines or bicyclic guanidines.

13 Claims, 1 Drawing Sheet

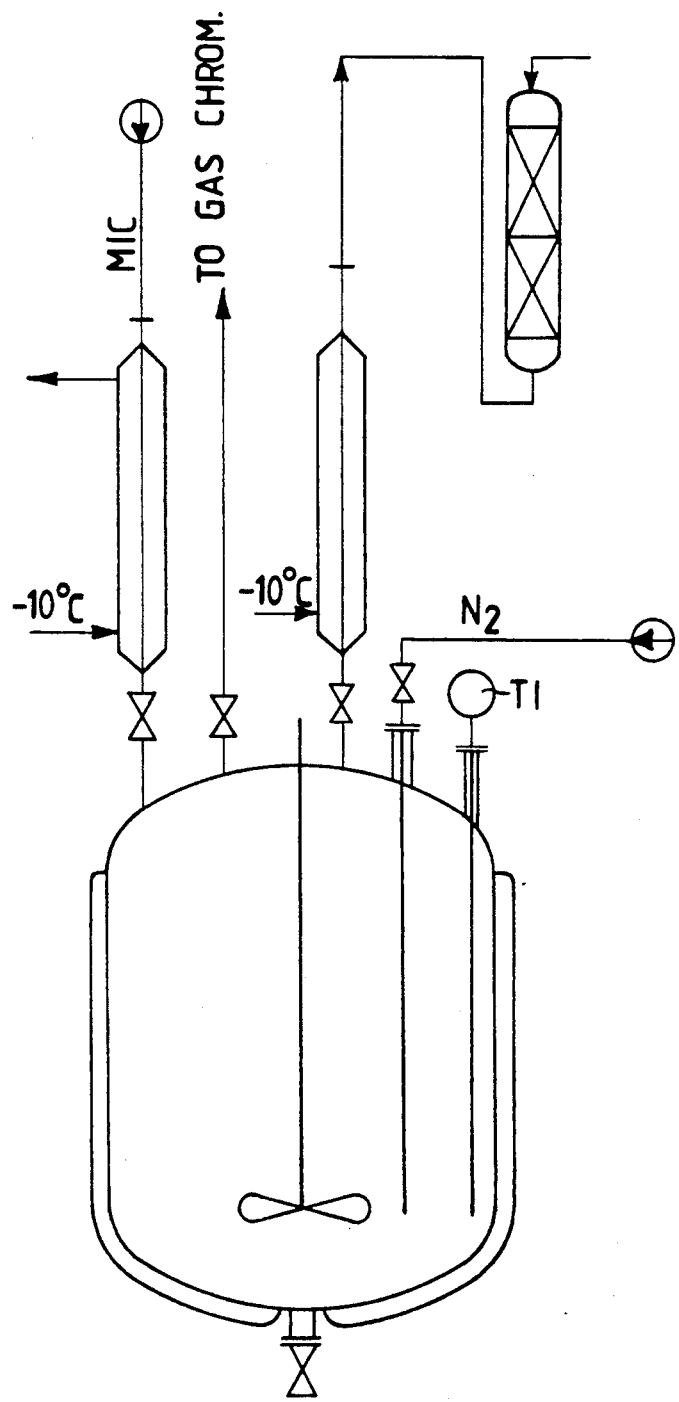

PROCESS FOR PRODUCING N-ALKYL-CARBAMATES

This is a continuation of Ser. No. 220,463, filed July 18, 1988, now abandoned.

The present invention relates to an improved process for producing N-alkyl-carbamates by means of the reaction of a phenol or of a naphthol with an alkyl isocyanate.

N-alkyl-carbamates are valuable products and many of them display an useful activity as plant disease control agents, such as, e.g., 2,3-dihydro-2,2-dimethylbenzofuran-7-yl N-methyl-carbamate (known as CARBOFURAN), 1-naphthyl N-methyl-carbamate (known as CARBARYL) and 2-isopropoxy-phenyl N-methyl-carbamate (known as PROPOXUR).

N-alkyl-carbamates are obtained, according to the prior art, by reacting an alkyl isocyanate, in particular methyl isocyanate, with a phenol or a naphthol, by operating in an inert organic solvent and in the presence of a basic catalyst. For this purpose, reference is made to R. J. Kuhr and H. D. Dorough, "Carbamates Insecticides; Chemistry, Biochemistry and Toxicology", CRC Press (1977) and to the disclosure of U.S. Pat. No. 4,390,710 and of European patent application Publication No. 200.249.

The catalysts used in said reaction have a basic nature, and are normally selected from tertiary amines (e.g., triethylamine and triisopropylamine); heterocyclic bases (e.g., pyridine, 4-dimethyl-amino-pyridine and N-methyl-imidazole); alkali-metal alkoxides (e.g., sodium methoxide and sodium ethoxide); alkali-metal carbonates (e.g., sodium carbonate); and derivatives of such metals as tin and titanium (e.g., dibutyl-tin dilaurate and dibutyl-tin diacetate).

The preferred catalysts are the tertiary amines and tin derivatives.

In practice, the reaction between a phenol or a naphthol and an alkyl-isocyanate is carried out in the presence of said catalysts, by operating at relatively low temperatures, in an organic solvent, and using a mutual stoichiometric ratio of the reactants, or a slight excess of the phenol or naphthol over the stoichiometric amount. Under these conditions, the reaction proceeds regularly, with high yields to the useful reaction product. The drawback which affects said reaction consists in the long times required for completing, or substantially completing, the same reaction, in particular in order to reduce to negligibly low values (less than 100 ppm—parts per million by weight) the residual alkyl isocyanate content in the reaction medium.

Such a matter of fact constitutes a disadvantage from both standpoints of process cheapness, and of the extremely high toxicity of alkyl isocyanates in general, and of methyl isocyanate in particular.

The present Applicant has found now that the drawbacks affecting the prior art can be overcome by means of the adoption of particular catalysts which enable unexpectedly high reaction speeds between the phenol or the naphthol and the alkyl-isocyanate to be reached. Therefore, according to the present invention, it results possible the concentration of the alky-isocyanate to be reduced to negligibly low values, by operating with short reaction times, in systems using stoichiometric, or approximately stoichiometric, amounts of the reactants.

In accordance therewith, the present invention relates to a process for preparing N-alkyl-carbamates by means of the reaction between a phenol or a naphthol and an alky-isocyanate, by operating in an inert organic solvent and in the presence of a catalyst, said process being characterized in that it takes place in the presence of a catalytic amount of a bicyclic amidine (I) or of a bicyclic guanidine (II) provided with a stretched tertiary nitrogen bonded to a ketoiminic carbon atom, and which can be represented by means of the formulae:

(I)

and

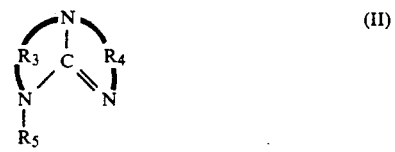
(II)

wherein:

$R_1$ and $R_2$ independently represent non-substituted or substituted alkylenic radicals containing from 3 to 5 carbon atoms with one or more ($C_1$–$C_5$)-alkyl or phenyl substituents;

$R_3$ and $R_4$ independently represent non-substituted or substituted alkylenic radicals containing 3 or 4 carbon atoms with one or more ($C_1$–$C_5$)-alkyl or phenyl substituents;

$R_5$ is a ($C_1$–$C_5$)-alkyl, or alkyl-aryl radical.

Specific examples of catalysts are:

1,5-diazabicyclo (4.3.0) non-5-ene

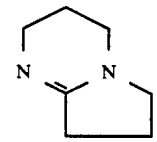

3-phenyl-1,5-diazabicyclo (4.3.0) non-5-ene

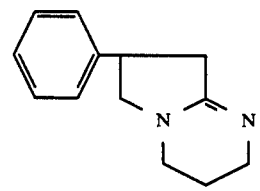

1,8-diazabicyclo (5.4.0) undec-7-ene

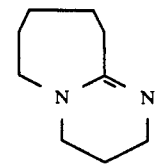

7-methyl-1,5,7-triazabicyclo (4.4.0) dec-5-ene

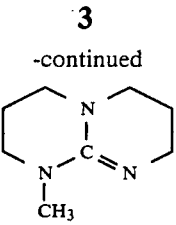

1,8-Diazabicylo (5.4.0) undec-7-ene can be prepared by making caprolactam and acrylonitrile react with each other (Michael reaction) and catalytically reducing the so obtained reaction product, as described by H. Oediger and H. Moller in Angew. Chem. 79, 53 (1967).

1,5-Diazabicyclo (4.3.0) non-5-ene can be prepared in a similar way by starting from butyrolactam.

Other amidines useful for the intended purpose are described in Tetrahedron Letters, 51, 5175-7 (1967).

The reaction between the phenol or naphthol and the alkyl-isocyanate can be represented by the following equation:

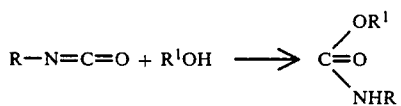

The alkyl-isocyanates (R—N=C=O) useful for the intended purpose are those wherein R represents an alkyl group containing from 1 to 4 carbon atoms, and preferably a methyl group.

Examples of $R^1OH$ compounds, useful for the intended purpose, are phenol; substituted phenol, with from 1 to 3 substituents, which may be either equal to, or different from, one another, selected from alkyl, alkoxy, alkylthio alkylamino, alcoxyalkylene, alkylthioalkylene, alkylaminoalkylene groups, wherein the alkyl group, which may be either linear or branched, contains from 1 to 5 carbon atoms (preferably from 1 to 3 carbon atoms) and the alkylene group contains 1 or 2 carbon atoms (it is preferably methylene); 1-naphthol; 2-naphthol; 2,3-dihydro-2,2-dimethyl-benzofuran-7-ol; 2,2-dimethyl-1,3-benzodioxol-4-ol; and 2-(1,3-dioxolan-2-yl)phenol.

Examples of preferred $R^1OH$ compounds for the purposes of the present invention are: 3,5-xylenol; 3,4-xylenol; 2-isopropyl-phenol; 2-isopropoxy-phenol; 2-(ethylthiometyl)-phenol; 2-cresol; 3-isopropyl-5-methylphenol; 4-methyl-thio-3,5-dimethyl-phenol; 4-dimethylamino-3-methyl-phenol; 1-naphthol; 2,3-dihydro-2,2-dimethylbenzofuran-7-ol; and 2,2-dimethyl-1,3-benzodioxol-4-ol.

According to the process of the present invention, the reaction is carried out in solution in an inert organic solvent and the solvents suitable for the intended purpose can be selected from aromatic hydrocarbons, such as benzene, toluene and xylene; ketones, such as acetone, methyl-ethyl-ketone and methyl-isobutyl-ketone; esters, such as ethyl acetate, dimethyl carbonate and diethyl carbonate; chlorinated aliphatic hydrocarbons, such as chloroform, methylene chloride, carbon tetrachloride and dichloroethane; and ethers, such as diethyl ether and tetrahydrofuran.

The reaction temperatures are not particularly critical, and can vary within the range of from 0° to 50° C.

Furthermore, the reaction is carried out with an equimolar or nearly equimolar ratio of the phenol or naphthol reactant to the alkyl-isocyanate reactant, in particular with ratios comprised within the range of from 1/1 to 1.1/1.

The amount of catalyst used for the reaction can generally vary within the range of from 0.0001 to 0.05 mol per each mol of the phenol or naphthol compound. The preferred catalyst amounts are comprised within the range of from 0.0005 to 0.02 mol per each mol of the phenol or naphthol compound.

The way how the reactants are placed into contact is not critic, however, in the preferred form of practical embodiment the reaction is carried out by dissolving the phenol or naphthol, besides the catalyst, in the selected organic solvent, and to the so obtained solution the alkyl isocyanate is gradually added until a molar ratio of the phenol or naphthol to said alkyl-isocyanate is reached, which is comprised within the above stated range of values.

A technique of such a kind is disclosed, e.g., in U.S. patent application No. 4,659,845.

By means of the catalysts of the present invention, rates of reaction between the phenol or naphthol and the alkyl-isocyanate are reached, which are generally from 100 to 1,000 times higher than those which can be obtained by means of the catalysts known in the prior art, with the molar catalyst concentration, and the other reaction conditions being the same.

In order to better evidence the activity of the catalysts according to the present invention, the values can be compared of the constants of rate of carbamate formation (Kabs) from 2,3-dihydro-2,2-dimethylbenzofuran-7-ol with methyl isocyanate, which are obtained by operating at 25° C. in toluene as the solvent, by using various concentrations of:

1,8-diazabicyclo (5,4,0) undec-7-ene (DBU),
1,5-diazabicyclo (5,4,0) non-5-ene (DBN) and
7-methyl-1,5,7-triazabicyclo (4,4,0) dec-5-ene (MTBD)
and of the catalyst known from the prior art triethylamine (TEA).

| DBU | Kabs |
|---|---|
| $2 \cdot 10^{-3}$ mol/liter | 5,63 liters · mol$^{-1}$ · min$^{-1}$ |
| $8 \cdot 10^{-3}$ mol/liter | 22.2 liters · mol$^{-1}$ · min$^{-1}$ |
| $2 \cdot 10^{-2}$ mol/liter | 27.7 liters · mol$^{-1}$ · min$^{-1}$ |
| DBN | Kabs |
| $1 \cdot 10^{-3}$ mol/liter | 4.5 liters · mol$^{-1}$ · min$^{-1}$ |
| $8 \cdot 10^{-3}$ mol/liter | 15.5 liters · mol$^{-1}$ · min$^{-1}$ |
| MIBD | Kabs |
| $3.4 \cdot 10^{-4}$ mol/liter | 12.5 liters · mol$^{-1}$ · min$^{-1}$ |
| $2.3 \cdot 10^{-3}$ mol/liter | 31.0 liters · mol$^{-1}$ · min$^{-1}$ |
| TEA | Kabs |
| $2.6 \cdot 10^{-3}$ mol/liter | $6.89 \cdot 10^{-3}$ liters · mol$^{-1}$ · min$^{-1}$ |
| $8.15 \cdot 10^{-3}$ mol/liter | $2.9 \cdot 10^{-2}$ liters · mol$^{-1}$ · min$^{-1}$ |
| $1.3 \cdot 10^{-2}$ mol/liter | $5.0 \cdot 10^{-2}$ liters · mol$^{-1}$ · min$^{-1}$ |

The following experimental examples are illustrative and not limitative of the present invention.

EXAMPLE 1

The equipment reported in the figure of the hereto attached drawing table is used, which comprises a reactor, equipped with a stirrer, which operates at atmospheric pressure and is connected through a condenser to a demister. The operating temperature is 20° C.

Methyl isocyanate is fed as a liquid (−10° C.) at flow rate of 6.93 g/hour, to the reactor, to which: 2,3-dihydro-2,2-dimethyl-benzofuran-7-ol (63.2 g), toluene (250 g) and 1,8-diazabicyclo (5.4.0) undec-7-ene (0.045 g) were previously charged.

The methyl isocyanate stream is fed for 3 hours. After this time period, the flow is discontinued and the reactor is separated from the feed line.

The residual amount of methyl isocyanate in the solution is determined at regular time intervals, by means of the chromatography of a constant nitrogen stream saturated, at room temperature, with methyl isocyanate and toluene (the reactor's vapour phase).

By means of a standard curve, the concentration of methyl isocyanate in the liquid phase is obtained.

The values of residual methyl isocyanate concentrations, expressed as parts per million parts by weight (MIC ppm) starting from the time of interruption of reactor feed are:

| Time (minutes) | MIC ppm |
|---|---|
| 0 | 1,600 |
| 10$^I$ | 160 |
| 15$^I$ | 57 |
| 20$^I$ | 21 |

By operating as previously disclosed, but using triethylamine as the catalyst, fed in an amount of 0.45 g (i.e., one order of magniture larger than of 1,8-diazabicyclo (5.4.0) undec-7-ene), the following results are obtained:

| Time (minutes) | MIC ppm | mol/liter |
|---|---|---|
| 0 | 25,500 | 0.402 |
| 10$^I$ | 22,000 | 0.347 |
| 15$^I$ | 20,100 | 0.318 |
| 20$^I$ | 18,800 | 0.296 |

EXAMPLE 2

The process is carried out as described in Example 1, by charging to the reactor:

| | |
|---|---|
| 2,3-dihydro-2,2-dimethyl-benzofuran-7-ol | 63.2 g |
| toluene | 250 g |
| 1,5-diazobicyclo (4.3.0) non-5-ene | 0.036 g |

The values of residual methyl isocyanate concentration are:

| Time (minutes) | MIC ppm | mol/liter |
|---|---|---|
| 0 | 1,120 | 0.017 |
| 5$^I$ | 150 | $2.37 \cdot 10^{-3}$ |
| 10$^I$ | 30 | $4.37 \cdot 10^{-4}$ |

EXAMPLE 3

The process is carried out as described in Example 1, by charging to the reactor:

| | |
|---|---|
| α-naphthol | 55.5 g |
| toluene | 500 g |
| 1,8-diazabicyclo (5.4.0) undec-7-ene | 0.174 g |

The values of residual methyl isocyanate concentration are:

| Time (minutes) | MIC ppm | mol/liter |
|---|---|---|
| 0 | 1,380 | 0.022 |
| 5$^I$ | 352 | $5.5 \cdot 10^{-3}$ |
| 10$^I$ | 120 | $1.9 \cdot 10^{-3}$ |
| 15$^I$ | 40 | $6 \cdot 10^{-4}$ |

We claim:

1. A process for preparing N-alkyl-carbamates by reacting a phenol or a naphthol and an alkyl-isocyanate in an inert organic solvent and in the presence of a catalyst, wherein said catalyst is a bicyclic amidine (I) or a bicyclic guanidine (II), containing a stretched tertiary nitrogen bonded to a ketoiminic carbon atom, and which is represented by the following formulae:

and

wherein:
$R_1$ and $R_2$ independently represent non-substituted or substituted alkylenic radicals containing from 3 to 5 carbon atoms with one or more ($C_1$-$C_5$)-alkyl or phenyl substituents;

$R_3$ and $R_4$ independently represent non-substituted or substituted alkylenic radicals containing 3 or 4 carbon atoms with one or more ($C_1$-$C_5$)-alkyl or phenyl substituents; and $R_5$ is a ($C_1$-$C_5$)-alkyl, or an alkyl-aryl radical.

2. The process according to claim 1, wherein said catalyst is selected from:
1,5-diazabicyclo (4.3.0) non-5-ene;
3-phenyl-1,5-diazabicyclo (4.3.0) non-5-ene;
1,8-diazabicyclo (5.4.0) undec-7-ene; and
7-methyl-1,5,7-triazabicyclo (4.4.0) dec-5-ene.

3. The process according to claim 1, wherein said catalyst is present in an amount within the range of from 0.0001 to 0.05 mol per each mol of phenol or naphthol.

4. The process according to claim 3, wherein said catalyst is present in an amount within the range of from 0.0005 to 0.02 mol per each mol of phenol of naphthol.

5. The process according to claim 1, wherein said phenol or naphthol is selected from phenol; phenol substituted with from 1 to 3 substituents which may be the same or different from one another, and selected from $C_1$-$C_5$-alkyl, $C_1$-$C_5$-alkoxy, $C_1$-$C_5$-alkylthio, $C_1$-$C_5$-alkylamino, $C_1$-$C_5$-alkoxy-$C_1$-$C_2$-alkylene, $C_1$-$C_5$-alkyl-thio-$C_1$-$C_2$-alkylene, and $C_1$-$C_5$-alkyla-mine-$C_1$-$C_2$-alkylene groups wherein the alkyl group can be linear or branched.

6. The process according to claim 1, wherein said phenol or naphthol is selected from: 3,4-xylenol; 3,5-xylenol; 2-isopropyl-phenol; 2-isopropoxy-phenol; 2-(ethylthiometyl)phenol; 2-cresol; 3-isopropyl-5-methyl-phenol; 4-methyl-thio-3,5-dimethyl-phenol; 4-dimethyl-amino-3-methyl-phenol; 1-naphthol; 2,3dihydro-2,2- dimethylbenzofuran-7-ol; and 2,2-dimethyl-1,3-benzodioxol-4-ol.

7. The process according to claim 1, wherein said alkyl-isocyanate contains from 1 to 4 carbon atoms in the alkyl group.

8. The process according to claim 7, wherein said alkyl isocyanate is methyl isocyanate.

9. The process according to claim 1, wherein said solvent is selected from aromatic hydrocarbons, ketones, esters, chlorinated hydrocarbons and ethers.

10. The process according to claim 1, wherein said reaction is carried out at a temperature within the range of from 0° C. to 50° C.

11. The process according to claim 1, wherein said reaction is carried out with a molar ratio of the phenol or naphthol to the methyl-isocyanate within the range of from 1/1 to 1.1/1.

12. The process according to claim 5 wherein the alkyl group contains from 1 to 3 carbon atoms.

13. The process according to claim 1 wherein the naphthol or phenol group is selected from 1-naphthol; 2-naphthol; 2,3-dihydro-2,2-dimethylbenzofuran-7-ol; 2,2-dimethyl-1,3-benzodioxol-4-ol; and 2-(1,3-dioxolan-2-yl)-phenol.

* * * * *